US007993293B2

(12) United States Patent
Leatt

(10) Patent No.: US 7,993,293 B2
(45) Date of Patent: *Aug. 9, 2011

(54) NECK BRACE

(75) Inventor: Christopher James Leatt, Constantia (ZA)

(73) Assignee: XCEED Holdings CC, Cape Town (ZA)

( * ) Notice: Subject to any disclaimer, the term of this patent is extended or adjusted under 35 U.S.C. 154(b) by 222 days.

This patent is subject to a terminal disclaimer.

(21) Appl. No.: 11/440,576

(22) Filed: May 25, 2006

(65) Prior Publication Data
US 2007/0010771 A1 Jan. 11, 2007

Related U.S. Application Data

(63) Continuation of application No. PCT/ZA2004/000148, filed on Nov. 26, 2004.

(30) Foreign Application Priority Data

Nov. 26, 2003 (ZA) .................................. 2003/9174

(51) Int. Cl.
*A61F 5/00* (2006.01)
*A42B 1/24* (2006.01)
(52) U.S. Cl. .................................. 602/18; 602/5; 2/422
(58) Field of Classification Search .................. 602/17, 602/18, 5; 128/845, 846, 870, DIG. 23; D24/191; 2/422
See application file for complete search history.

(56) References Cited

U.S. PATENT DOCUMENTS

| 2,820,455 | A | 12/1953 | Hall |
| 3,514,784 | A | 6/1970 | McDavid |
| 3,601,123 | A | 8/1971 | McFarland |
| 3,724,452 | A | 4/1973 | Nitschke |
| 3,765,029 | A | 10/1973 | Germain |
| 3,765,412 | A | 10/1973 | Ommaya et al. |
| 3,855,631 | A | 12/1974 | Ettinger |
| 3,878,561 | A | 4/1975 | Winiecki |
| 4,274,161 | A | 6/1981 | Littler |
| 4,319,362 | A | 3/1982 | Ettinger |
| 4,324,003 | A * | 4/1982 | Johnston ........................... 2/468 |
| 4,338,685 | A | 7/1982 | LaPorta, Jr. |
| 4,383,523 | A | 5/1983 | Schurman |
| 4,449,251 | A | 5/1984 | Gauthier |

(Continued)

FOREIGN PATENT DOCUMENTS
AU 2004293118 A1 6/2005
(Continued)

OTHER PUBLICATIONS

Radek et al., "Conception of the Cervico-brachial Protector for Motorcycle Drivers," Neurol Nerochir Pol. 2000; 34(6) (suppl): 94-106.

(Continued)

*Primary Examiner* — Kim M Lewis
(74) *Attorney, Agent, or Firm* — Kilpatrick, Townsend & Stockton, LLP

(57) ABSTRACT

A neck brace (10) is disclosed which comprises two sections (12, 14) which are releasably connected to one another along a split line (18). The ring has upwardly facing surfaces (30, 76.1, 20.2) which limit tilting movement of a helmeted head in all directions. The brace further has a column (68, 70) which extends downwardly from the ring for transferring loads to the wearer's back on each side of the spine.

51 Claims, 6 Drawing Sheets

U.S. PATENT DOCUMENTS

| | | | |
|---|---|---|---|
| 4,501,023 A | 2/1985 | Bilberry | |
| 4,638,510 A | 1/1987 | Hubbard | |
| 4,643,174 A | 2/1987 | Horiuchi | |
| 4,821,339 A | 4/1989 | Fair | |
| 4,996,720 A * | 3/1991 | Fair | 2/462 |
| 5,003,968 A | 4/1991 | Mars | |
| 5,009,223 A | 4/1991 | DeFonce | |
| 5,230,698 A | 7/1993 | Garth et al. | |
| 5,371,905 A | 12/1994 | Keim | |
| 5,388,278 A * | 2/1995 | Taniuchi | 2/422 |
| 5,404,590 A | 4/1995 | Monica, Jr. | |
| 5,437,613 A | 8/1995 | Reggio et al. | |
| 5,444,870 A | 8/1995 | Pinsen | |
| 5,483,698 A | 1/1996 | Douglas, Jr. | |
| 5,517,699 A | 5/1996 | Abraham, II | |
| 5,531,669 A | 7/1996 | Varnau | |
| 5,546,601 A | 8/1996 | Abeyta | |
| 5,546,609 A | 8/1996 | Rush, III | |
| 5,891,069 A | 4/1999 | Moffett | |
| 5,930,843 A | 8/1999 | Kelly | |
| 6,058,517 A * | 5/2000 | Hartunian | 2/468 |
| 6,067,665 A | 5/2000 | DePalma et al. | |
| 6,253,389 B1 | 7/2001 | Scaglione | |
| 6,481,026 B1 | 11/2002 | McIntosh | |
| 6,591,430 B1 | 7/2003 | Sledge | |
| 6,854,134 B2 * | 2/2005 | Cleveland | 2/422 |
| 6,872,188 B2 | 3/2005 | Caille et al. | |
| 6,874,170 B1 | 4/2005 | Aaron | |
| 7,141,031 B2 | 11/2006 | Garth et al. | |
| 2002/0169401 A1 * | 11/2002 | Walpin | 602/18 |
| 2003/0060744 A1 | 3/2003 | Caille et al. | |
| 2005/0113728 A1 * | 5/2005 | Heinz et al. | 602/18 |

FOREIGN PATENT DOCUMENTS

| | | |
|---|---|---|
| CA | 1204034 A1 | 5/1986 |
| DE | 2717712 A1 | 10/1978 |
| DE | 2921353 | 12/1980 |
| DE | 3136466 | 4/1983 |
| DE | 29521373 U1 | 3/1997 |
| DE | 19545299 | 6/1997 |
| DE | 20006084 U1 | 7/2001 |
| EP | 81105116 A1 | 1/1982 |
| GB | 779 717 | 7/1957 |
| GB | 2126485 A * | 3/1984 |
| JP | 2002-303988 | 10/2002 |
| JP | 08-510300 | 4/2008 |
| WO | 91/03178 | 3/1991 |
| WO | 97/06702 | 2/1997 |
| WO | 98/09545 | 3/1998 |
| WO | 9938401 | 8/1999 |
| WO | 01/25088 | 4/2001 |
| WO | 02089620 | 11/2002 |
| WO | 03/015555 | 2/2003 |
| WO | WO 03077793 | 9/2003 |
| WO | 03/092561 | 11/2003 |
| WO | 2006/023044 | 3/2006 |
| WO | 2007/120764 | 10/2007 |
| WO | 2008/050307 | 5/2008 |
| WO | 2008/105010 | 9/2008 |

OTHER PUBLICATIONS

White, Augustus A. and Panjabi, Manohar M., "Clinical Biomechanics of the Spine," 2nd Edition, Lippincott, 1990.
"Cowboy Collar" promoted and sold by manufacturer McDavid Inc. and their distributors, http://web,archive.org/web/20050428112624/mcdavidusa.com/cowboycollar.html.
Gordon et al., "Effects of Football Collars on Cervical Hyperextension and Lateral Flexion," Journal of Athletic Training 38(3), pp. 209-215.
Cross et al., "Training and Equipment to Prevent Athletic Head and Neck Injuries," Clinics in Sports Medicine, vol. 22, Issue 3, pp. 639-667.
Naylor et al., "Abstract: Analysis of a Neck Brace for Rugby," Australian Journal of Science Medicine in Sport, 20, 24, 1988.
Pearl et al., "Neck Motion in the High School Football Player," The American Journal of Sport Medicine, 7:231-233, 1979.
Hovis et al., "An Evaluation of Cervical Orthoses in Limiting Hyperextension and Lateral Flexion in Football," Medicine and Science in Sports and Exercise, vol. 26(7), pp. 872-876.
Markey et al. , "Upper Trunk Brachial Plexopathy: The Stinger syndrome," The American Journal of Sports Medicine, vol. 21, No. 5, pp. 650-655.
International Search Report, PCT/ZA2004/000148, mailed Jul. 5, 2005.
International Preliminary Report on Patentability, PCT/ZA2004/000148, mailed May 29, 2006.
Written Opinion of the International Searching Authority, PCT/ZA2004/000148, mailed Jul. 5, 2005.
Examiner's first report, Australian Patent Application No. 2004293118, mailed Feb. 11, 2008.
Response to Examiner's first report, Australian Patent Application 2004293118, filed Jan. 29, 2009.
Statement of Grounds and Particulars filed in opposition to Australian Patent Application No. 2004293118, filed Aug. 26, 2009.
Statement of Grounds and Particulars filed in opposition to Australian Patent Application No. 2004293118, filed Feb. 26, 2010.
Statutory Declaration of Antony John Fowler Ward filed in opposition to Australian Patent Application No. 2004293118, signed Feb. 26, 2010.
Statutory Declaration of Dr. Thomas J. Gibson filed in opposition to Australian Patent Application No. 2004293118, Signed Mar. 24, 2010.
Notice of Reasons for Rejection, Japanese Patent Application No. P2006-541524, mailed Oct. 20, 2009.
Requisition by The Examiner, Canadian Patent Application No. 2,547,885, mailed Nov. 17, 2009.
Communication pursuant to Article 94(3) EPC, EP Application No. 09165346.9, mailed Jan. 8, 2010.
European Search Report, EP Application No. 09165346, mailed Sep. 23, 2009.
Communication pursuant to Article 94(3) EPC, EP Application No. 04816084.0, mailed Dec. 20, 2007.
Response to Communication mailed Dec. 20, 2007, in EP Application No. 04816084.0, filed Apr. 15, 2008.
Communication pursuant to Article 94(3) EPC, EP Application No. 04816084.0, mailed Oct. 10, 2008.
Response to Communication mailed Oct. 10, 2008, in EP Application No. 04816084.0, filed Jan. 14, 2009.
Notification of First Office Action, Chinese Application No. 20040035072.4, mailed Aug. 17, 2007.
Decision on Rejection, Chinese Application No. 20040035072.4, mailed Nov. 28, 2008.
Request for Examination, Chinese Application No. 20040035072.4, filed Mar. 12, 2009.
Response to First Office Action, Chinese Application No. 20040035072.4, filed Dec. 29, 2007.
Response to Second Office Action, Chinese Application No. 20040035072.4, filed Oct. 13, 2008.
Notification of the Second Office Action, Chinese Application No. 20040035072.4, mailed Aug. 8, 2008.
Report of Substantive Examination, Indonesian Patent Application No. WO0200601467, mailed Dec. 30, 2008.
Office Action, Israeli Patent Application No. 175931, mailed May 21, 2009.
Response to Office Action mailed May 21, 2009, Israeli Patent Application No. 175931.
Notice of Examination Report, South Korean Patent Application No. 10-2006-7012173, mailed Apr. 30, 2007.
Notice of Examination Report, South Korean Patent Application No. 10-2006-7012173, mailed Jun. 13, 2008.
Response to Notice of Examination Report mailed Apr. 20, 2007, South Korean Patent Application No. 10-2006-7012173.
Response to Notice of Examination Report mailed Jun. 13, 2008, South Korean Patent Application No. 10-2006-7012173.
Substantive Examination Adverse Report, Malaysian Patent Application No. PI 20062407, mailed Aug. 1, 2009.
Claims as filed in Response to Substantive Examination Adverse Report mailed Aug. 1, 2009 in Malaysian Patent Application No. PI 20062407.

Official Action Regarding Patent Application, Norwegian Patent Application No. 20062971, mailed Jul. 17, 2008.

Memorandum in Response to Official Action Regarding Patent Application mailed Jul. 17, 2008, Norwegian Patent Application No. 20062971.

Examination Report, New Zealand Patent Application No. 548068, mailed Dec. 3, 2008.

Response to Examination Report mailed Dec. 3, 2008, New Zealand Patent Application No. 548068, filed May 7, 2009.

Notice of Allowance, Ukranian Patent Application No. 200607118, mailed Aug. 25, 2009.

PCT International Search Report for PCT/CH2008/052880 dated Dec. 18, 2008.

European Written Opinion and Search Report for EP 09 16 5346 dated Sep. 23, 2009.

Response to Communication under Article 94(3) EPC for EP 09165346.9, mailed Jun. 28, 2010, 7 pages.

Nahum, Alan M and Melvin, John W. (ed.), "Accidental Injury: Biomechanics and Prevention", Springer-Verlag, 2001, Chapter 15, pp. 324-373.

Facts and Arguments filed in opposition to EP Patent Application No. 04816084.0, filed Jan. 14, 2011, 8 pages.

Response to facts and Arguments filed in opposition to EP Patent Application No. 04816084, filed May 16, 2011, 5 pages.

* cited by examiner

NECK BRACE

This application is a continuation of international application PCT/ZA2004/000148 filed 26 Nov. 2004, published in English under PCT Article 21(2), which claims benefit from South African Application Serial No. 2003/9174 filed 26 Nov. 2003, the specifications of which are hereby incorporated herein by reference.

BACKGROUND OF THE INVENTION

1. Field of the Invention

This invention relates to relates to neck braces.

2. Description of the Related Art

A neck brace is generally used to support and immobilize the neck of the wearer after the wearer has sustained a neck injury.

The purpose of the neck brace of the present invention is to provide protection against most types of neck injuries such as fractures which may be sustained by a user, especially by a participant in a sport activity where there is a risk of serious neck injury such as high speed motor sports.

BRIEF SUMMARY OF THE INVENTION

According to a first aspect of the present invention there is provided a neck brace comprising a ring which fits around the wearer's neck, a column which depends from the ring at a position at the rear of the ring so that it extends down the wearer's back, and cushioning along the vertical edges of the column for transmitting to the wearer's back, on each side of the spine, impact loads which are imposed on the brace.

According to a second aspect of the present invention there is provided a neck brace which comprises a ring for fitting around the wearer's neck, an upper extension which protrudes from the ring in the rearward direction and a wall extending upwardly from said rearward extension for contacting the underside of the rear edge of a crash helmet and limiting tilting of the helmet in the rearward direction, a lower rearward extension, a column which depends from said lower rearward extension so that it extends down the wearer's back, and cushioning along the vertical edges of the column for transmitting to the wearer's back, on each side of the spine, impact loads which are imposed on the brace.

According to a third aspect of the present invention there is provided a neck brace comprising a ring which fits around the wearer's neck, the brace having an extension which protrudes from the ring in the rearward direction and a wall extending upwardly from said rearward extension for contacting the underside of the rear edge of a crash helmet and limiting tilting of the helmet in the rearward direction.

Said wall, in plan view, can be of curving configuration and extend across the rear of the brace and part of the way along each side of the brace, the part of the wall which extends across the rear of the brace being of substantially constant height and the parts of the wall at the sides of the brace decreasing in height with increasing distance from the part of the wall which extends across the brace.

Preferably said wall slopes in the rearward direction thereby to provide an upwardly facing inclined surface which is positioned to intercept tilting movement and also projection of the rear part of the helmet.

According to a fourth aspect of the present invention there is provided a neck brace comprising a ring which fits around the wearer's neck, a forward and downward extension from said ring, and cushioning on the underside of the extension for bearing on the wearer's chest and transmitting to the chest impact loads that are imposed on the brace.

According to a fifth aspect of the present invention there is provided a neck brace comprising a ring which fits around the wearer's neck, a forward extension of the ring providing an upwardly facing impact surface which, when the brace is used with a full face crash helmet, limits downward tilting of the helmet by contacting the underside of the face guard of the helmet.

According to a sixth aspect of the present invention there is provided a neck brace comprising a ring which fits around the wearer's neck, an upper forward extension of the ring providing an upwardly facing impact surface which, when the brace is used with a full face crash helmet, limits downward tilting of the helmet by contacting the underside of the face guard of the helmet, a lower forward extension of the ring, cushioning on the underside of the lower extension for bearing on the wearer's chest and transmitting to the chest impact loads that are imposed on the brace, and a wall joining the upper and lower forward extensions, the wall being hollow and bounded by a radially outer skin and a radially inner skin.

In the preferred form said upper extension is hollow and bounded by an upper skin and a lower skin, the hollow interior of the upper extension communicating with the space between said inner and outer skins of the joining wall.

Said ring can comprise a U-shaped front section and a U-shaped rear section, there being releasable latching means for fastening said sections to one another.

In one constructional form said column comprises a vertically extending bar depending from the ring, a plate wider than the bar secured to the bar and protruding laterally therefrom on each side thereof, said cushioning being carried by said plate.

The wall joining the upper and lower forward extensions can be fabricated so that it constitutes a fracture zone.

BRIEF DESCRIPTION OF THE DRAWINGS

For a better understanding of the present invention, and to show how the same may be carried into effect, reference will now be made, by way of example, to the accompanying drawings in which.

DETAILED DESCRIPTION

Figure 1:
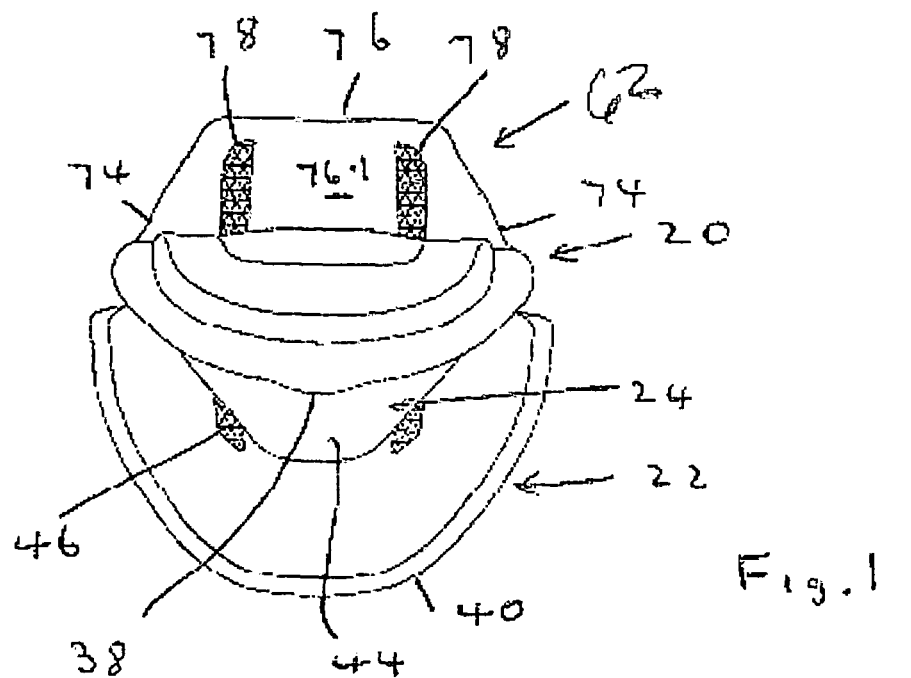
FIG. 1 is a front elevation of a neck brace according to the present invention.

The neck brace comprises a ring shaped to dissipate forces of axial loading, flexion, extension, lateral flexion and lateral rotation, while still affording the wearer's head a range of movement. A helmet may be locatable above an upper surface of the ring when it is worn by a wearer. The helmet is preferably a full face crash helmet such as is used in, for example, motorcycle racing or motocross racing.

The neck brace provides a way for helmet clad wearers, especially those participating in high speed motor sports such as motorcycle racing, to have a high degree of protection against neck trauma by virtue of the brace being shaped to dissipate forces of axial loading, flexion, extension, lateral flexion and lateral rotation, while still affording the wearer a reasonable range of movement.

More specifically, a helmet worn by a wearer is located above the upper surface of the neck brace with a clearance between the lower part of the helmet and an upwardly facing surface. This permits the head a necessary degree of freedom of movement whilst ensuring that there is contact between the helmet's lower edge and the upwardly facing surface of the brace, thereby inhibiting further movement of the head, before the movement of the head is sufficient to cause neck damage.

The neck brace may comprise flexible cushioning material and less flexible strength imparting material. The flexible material may be, for example, rubber, sponge, foam rubber or high density polystyrene, and may provide the inner lining of the neck brace which is the inner side located nearest the neck of the wearer. The less flexible material may be, for example, carbon fiber, kevlar, titanium or aluminum, and may include a structure of titanium struts hidden within the brace to provide additional strength.

The neck brace illustrated in FIGS. 1 to 6 is generally designated 10 and comprises a front section 12 and a rear section 14 which are secured together to form a ring which goes around the wearer's neck. The connection can comprise two spring loaded latches or, preferably, one spring loaded latch 16.1 and a hinge 16.2. The split line between the front and rear sections is designed 18.

The front section 12 is U-shaped in plan and includes a hollow top flange 20 and a solid bottom flange 22 which are joined by a composite wall 24.

The top flange has an upper face which is stepped along the curving line 28 to provide an upwardly facing outer surface 30 and an upwardly facing inner surface. The outer surface 30 is above the inner surface. The inner surface is not visible in the drawings as it is concealed by a piece of horse-shoe shaped cushioning 32. The cushioning 32 is releasably secured to said inner surface by, for example, a strip of the "hook and loop" fastener (not shown), which is generally sold under the trade mark VELCRO®, fixed to the transverse portion of the inner, lower surface. The cushioning 32 protrudes above the surface 30.

The top flange 20, when its rear end is viewed along the split line 18, slopes in such a manner that the inner edge of the inner, lower surface is below its outer edge, and the inner edge of the surface 30 is below its outer edge. The front, transversely extending portion of the surface 30 is wider in the radial direction than the side portions of this surface and curves upwardly (see particularly FIG. 6) to form a forwardly facing lip designated 38.

The bottom flange 22 is wider than the top flange 20 and protrudes beyond the top flange both laterally and in the forward direction. The underside of the flange 22 has a layer of cushioning material 40 secured thereto. The layer 40, when the brace 10 is being worn, is in contact with the part of the wearer's chest which is immediately below the neck.

The wall 24 which joins the flanges 20, 22 is of double skin hollow construction at the forward end of the section 12 and of single skin construction towards the free ends of the limbs of the U-shaped section 12.

The inner edges of the flanges 20, 22 of the section 12 are joined by a curving inner skin 42 of the wall 24. The outer skin of the wall is designated 44 and extends from the underside of the top flange 20 to the top surface of the bottom flange 22.

The bottom flange 22 is constituted by a single skin whereas the top flange 20, as mentioned above, is of hollow construction. The upper skin of the top flange 20 provides the surface 30, the surface to which the cushioning 32 is fixed and the top surface of the lip 38. The lower skin forms the underside of the lip 38 and merges with the outer skin 44 of the wall 24.

Thus the forward part of the neck brace is hollow, the internal space being bounded by the top and bottom flanges 20, 22 and by the skins of the wall 24. The hollow lip 38 forms a forward extension of the space between the skins 42, 44 and the flanges 20, 22.

Air vents (not shown) are provided in the skin 44 and further air vents 46 are provided in the flange 22. These vents all communicate with said internal space and allow air to flow through the hollow front section of the brace.

The free edges of the lower flanges are stepped down at 50 (see FIG. 2) to allow the two sections 12, 14 to be overlapped as will be described in more detail later.

The rear section 14 includes top and bottom flanges 52, 54 which form continuations of the top and bottom flanges 20, 22 of the front section 12 when the sections are joined.

The top flange 52 is configured with a step in it so that its upper surface has a radially inner part which is lower than the radially outer part. The radially outer part is designated 56 and the radially inner part has cushioning 58 secured to it by one or more strips of VELCRO®. The flange 52 is hollow and bounded by an upper skin constituting the stepped top surface of the flange and by a lower skin.

The rear of the brace is constituted by a first wall designated 60 and a second wall designated 62.

The bottom flanges 54 curve downwardly at their rear ends to merge with the wall 60. Air vents 64 are provided in the wall 60 and there is a vertically extending recess 66 in the centre of the rearwardly facing surface of the wall 60.

A bar 68 has its upper end in the recess 66 and is screwed to the wall 60. A plate 70 which is wider than the bar 68 is secured to the bar 68 by screws or other suitable means and protrudes in both horizontal directions beyond the bar 68. A U-shaped pad 72 of cushioning material is secured to the forwardly facing surface of the plate 70. The bar 68 and plate 70 constitute a column.

A wedge shaped shim (not shown) can be fitted between the bar 68 and the wall 60 so as to cause the bar to adopt a non-vertical orientation. Alternatively, two wedge shape shims in face-to-face contact can be used to displace the bar 68 rearwardly with respect to the wall 60 whilst leaving it vertical.

Shims can also be used between the bar 68 and plate 70 so as to angle the plate 70 with respect to the bar, or displace it rearwardly with respect to the bar.

The wall 62 constitutes an upward extension of the part 56 of the flange 52. The wall 62, in plan, has side sections 74 of generally triangular shape which increase in height towards the zones where they merge with a transverse section 76 of the wall 62. The section 76 slopes in the rearward direction to provide a surface 76.1 (see FIG. 1) and has two mesh covered air vents 78 in it. On its forwardly facing surface the section 76 has two cushioning pads 80 and there are further cushioning pads 82 on the inner faces of the sections 74.

Pads 88 of cushioning material are provided on the underside of the flanges 54.

Figure 2:
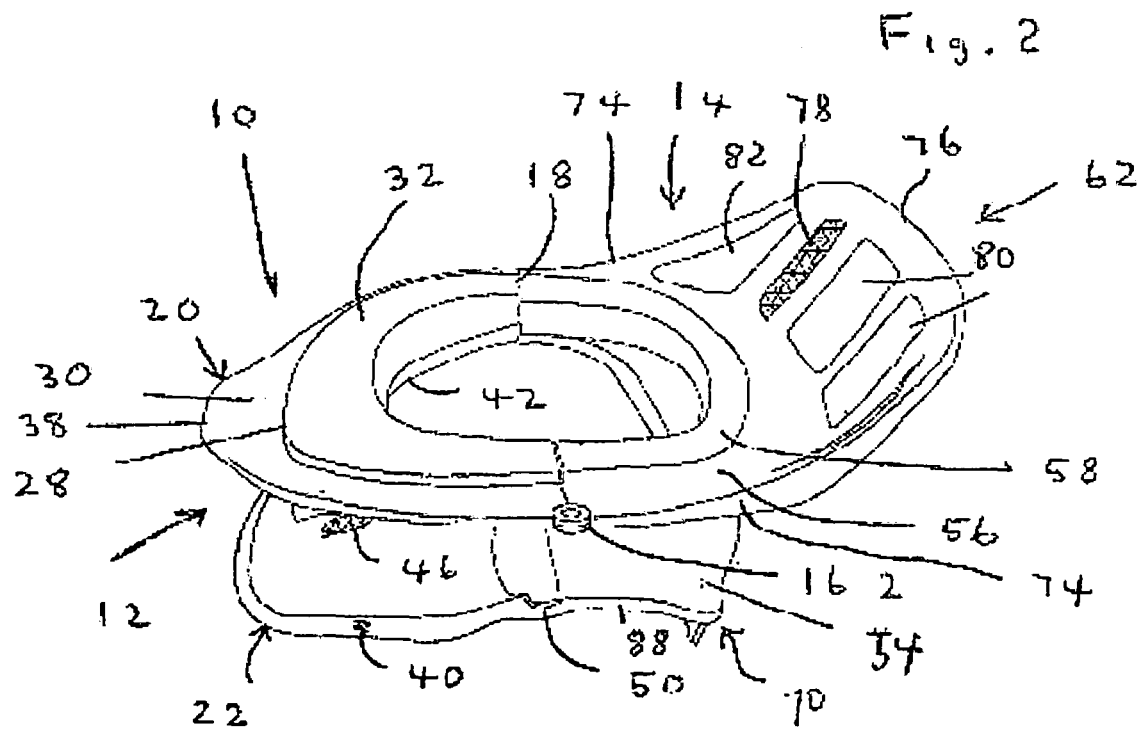
FIG. 2 is a pictorial view of the neck brace.
Figure 3:
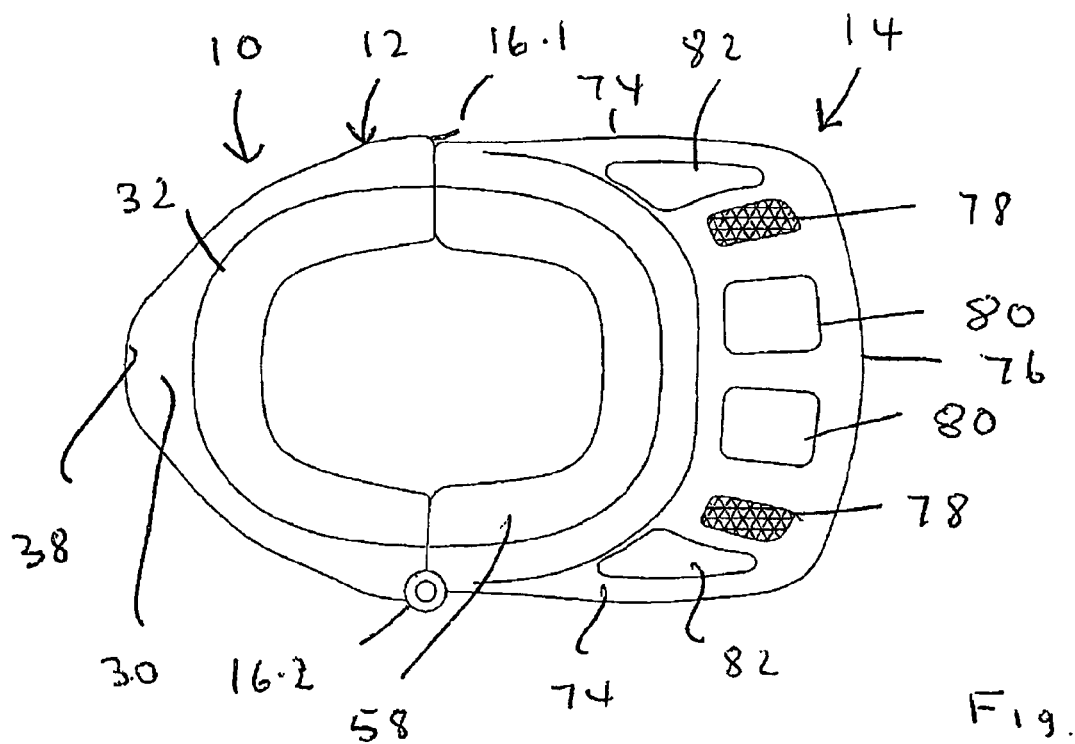
FIG. 3 is a top plan view of the neck brace.
Figure 4:
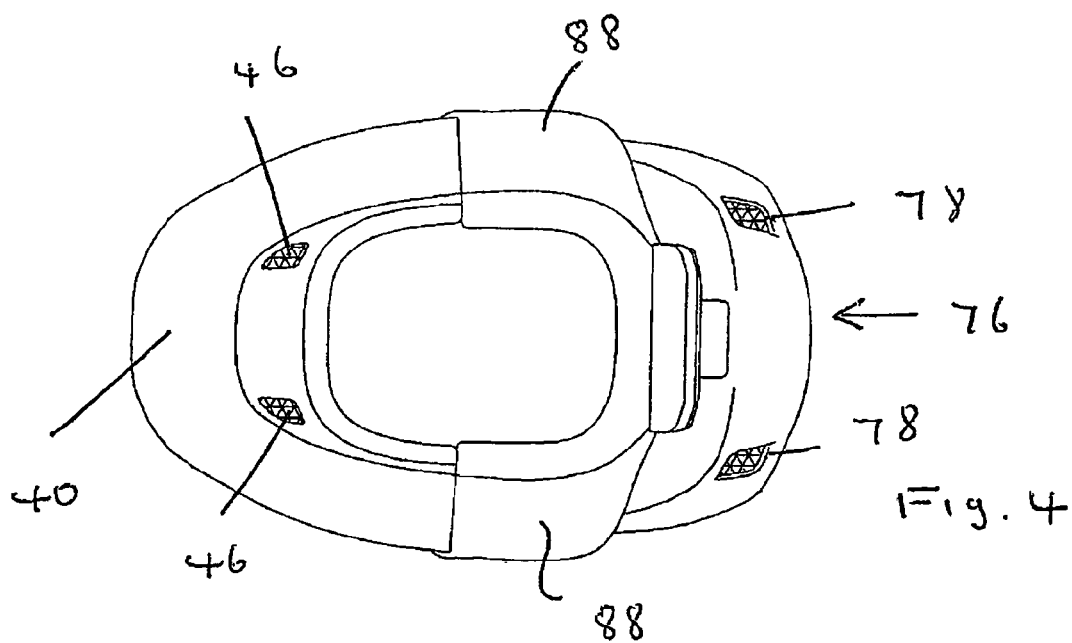
FIG. 4 is an underneath plan view of the neck brace.
Figure 5:
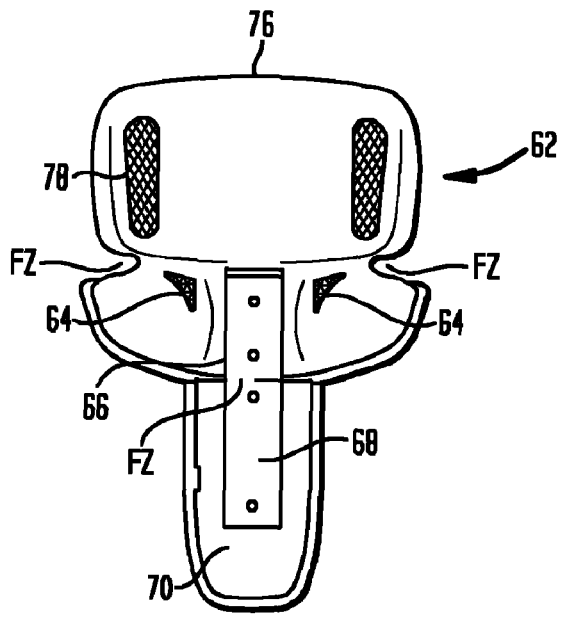
FIG. 5 is a rear elevation of the neck brace.
Figure 6:
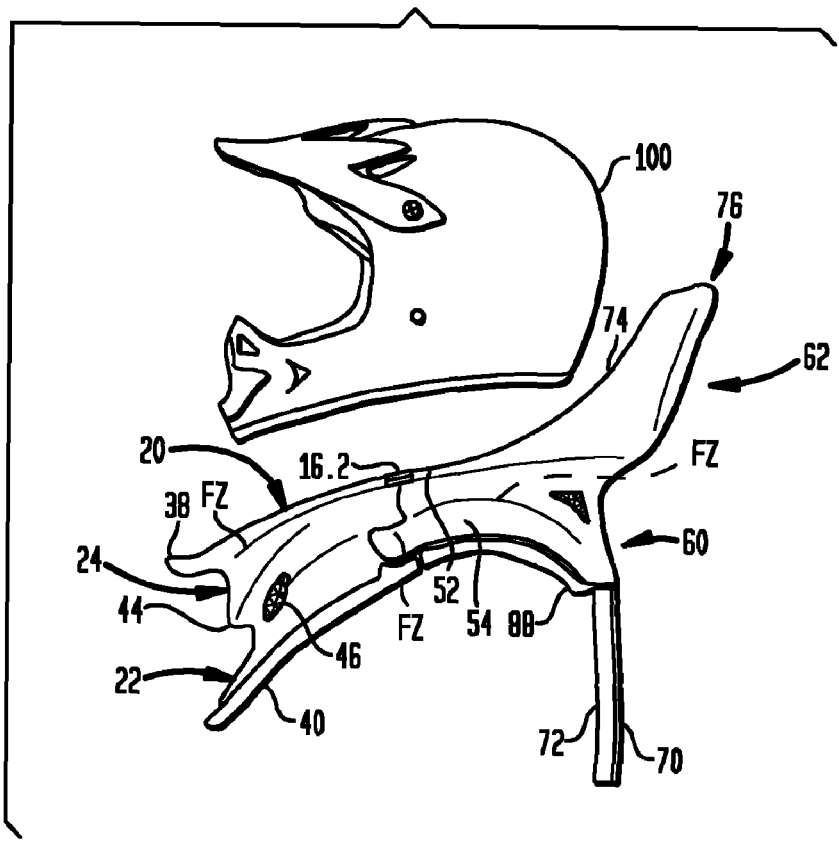
FIG. 6 is a side elevation of the neck brace.
Figure 7:
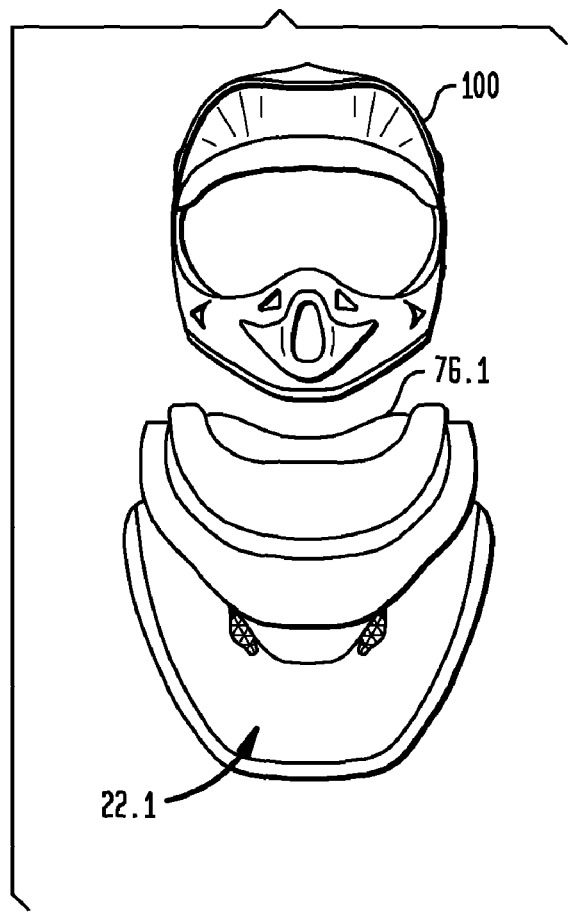
FIG. 7 is a front elevation of a further neck brace according to the present invention.
Figure 8:
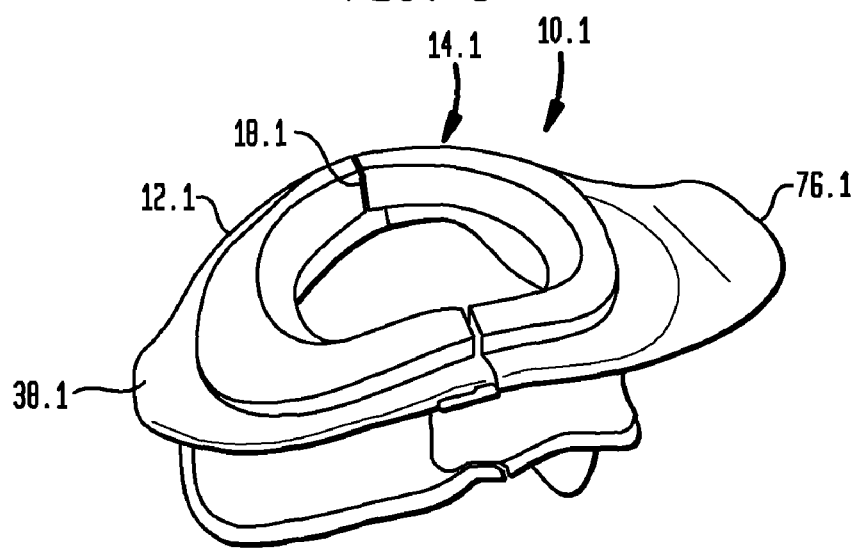
FIG. 8 is a pictorial view from one side and above of the brace of FIG. 7.
Figure 9:
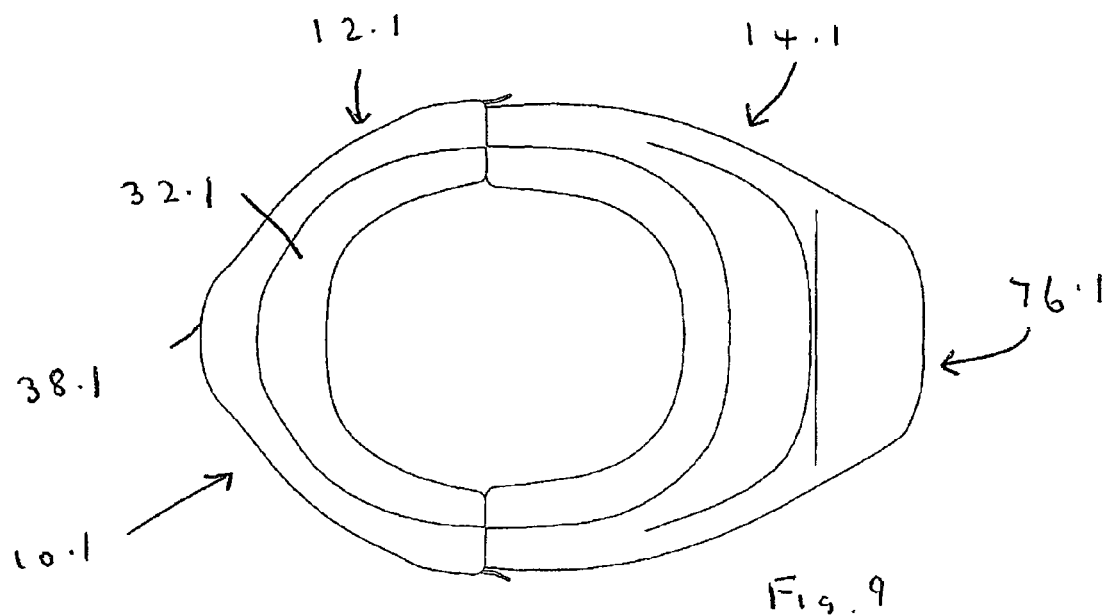
FIG. 9 is a top plan view of the neck brace of FIG. 7.
Figure 10:
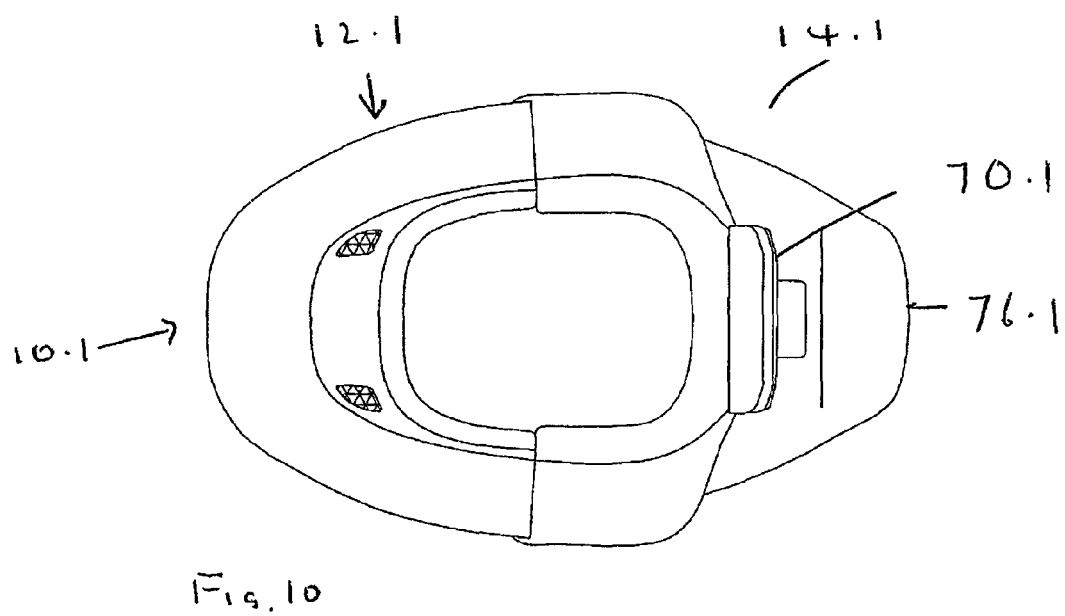
FIG. 10 is an underneath plan view of the neck brace of FIG. 7.
Figure 11:
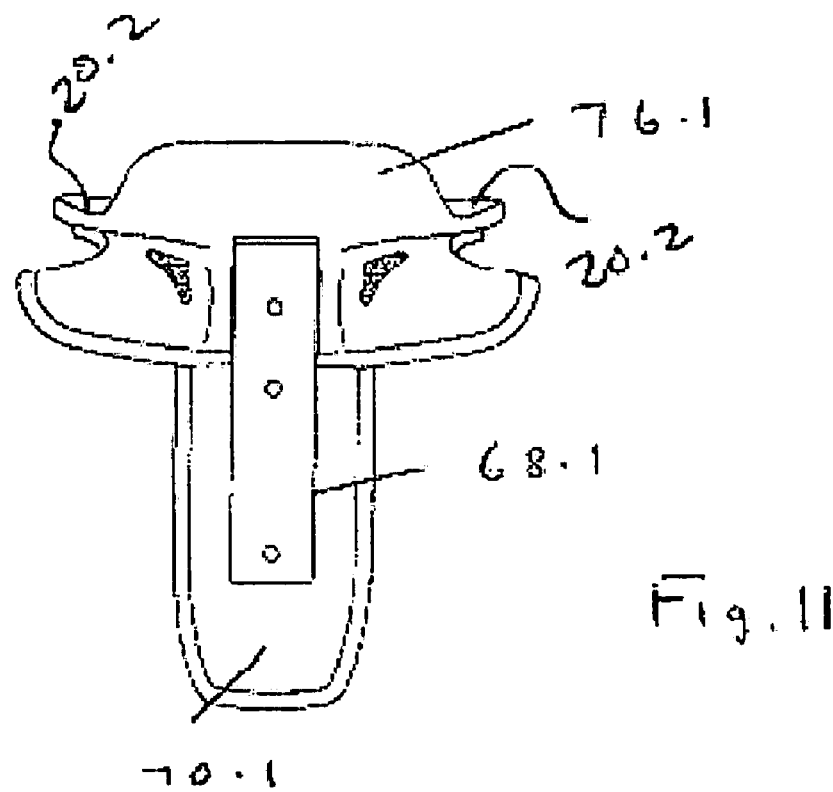
FIG. 11 is a rear elevation of the brace of FIG. 7.

The forward edges of the flanges 54 are configured so that they overlap with the rear edges of the flanges 22 (see FIG. 2).

The latch 16.1 is mounted on the section 14 and comprises a spring loaded locking bar which is in a socket of the flange 54 and can be manually displaced by an actuating element external of the flange. A tang (not shown) is secured to the section 12 and enters the socket containing the locking bar when the sections 12 and 14 are being joined. The tang has an angled slot in its side edge. The tang cams the locking bar to one side against spring action until the bar enters the angled slot. Only by manually displacing the locking bar out of the slot can the sections 12, 14 be separated.

The brace provides maximum protection when worn with a so called full face helmet. Such a helmet has a continuous lower edge which extends around the wearer's head at a level which is just below the chin. The gap between the helmet's lower edge and the upwardly facing surface of the neck brace allows the head some freedom of movement. However, this movement is restricted and after movement of the head relative to the body which is insufficient to cause neck damage, further relative movement is prevented as the gap closes up and the lower edge of the helmet strikes the upwardly facing surface. This enables flexion and extension of the head as well as lateral flexion and axial loading to be dissipated. Insofar as lateral rotation is concerned, this is inhibited by a strap which extends between the brace and the helmet. This strap causes lateral rotation of the head to be converted into flexion before the rotation is sufficient to cause neck damage.

The top edge and the inclined forward face 76.1 of the wall section 76 lie close to the wearer's crash helmet 61 and limit and limit both projection and rearward tilting movement of the head. The column constituted by the bar 68 and plate 70 transmits, via the pad 72, impact loads to the wearer's back. These loads are imposed not on the spine but on two zones lying one on each side of the spine.

The top flange 20 of the front section lies below the lower rim of the helmet 61 of the full face type and thus limits forward tilting motion of a helmeted head. The front part of the flange 22 lies on the wearer's chest and transmits loads to it through the cushioning 40 on the underside of the flange 22.

Most of the features of the brace of FIGS. 7 to 12 are common to it and to the brace of FIGS. 1 to 6. Like parts have been designated with like references to which the suffix ".1" has been added.

Figure 12:
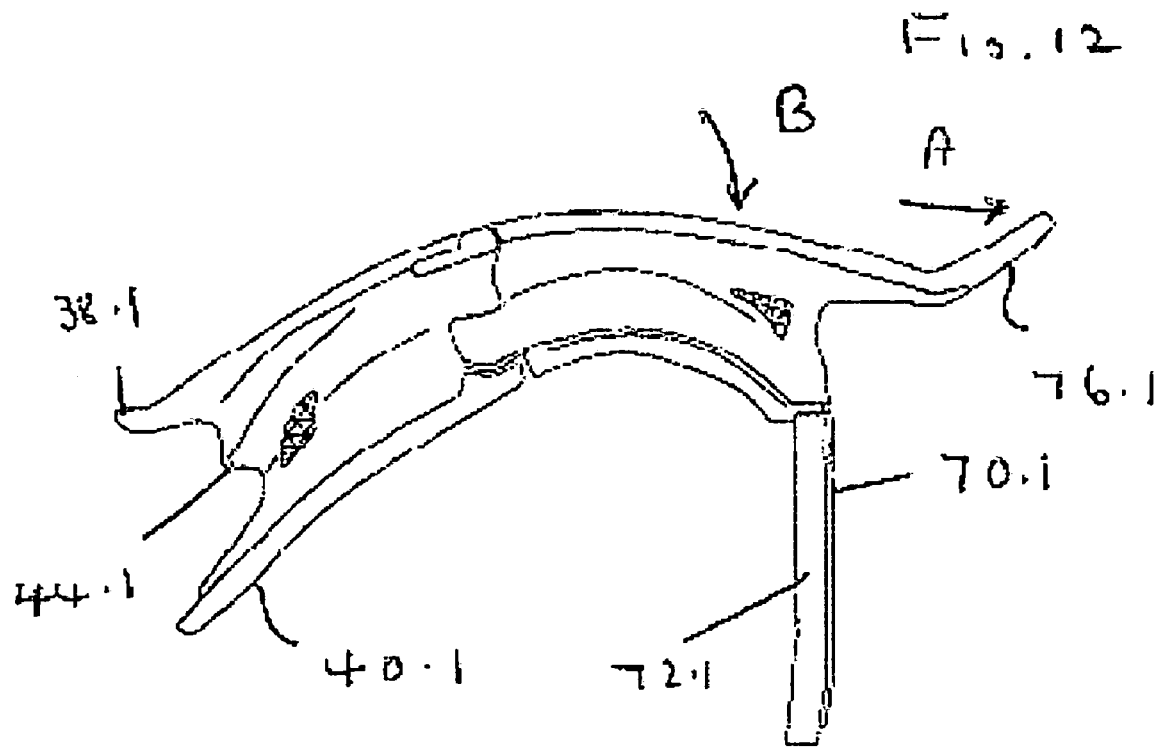
FIG. 12 is a side elevation of the brace of FIG. 7.

The most significant difference between the two braces is that the wall section 76 of FIGS. 1 to 6 is of far smaller height as can best be seen in FIG. 12. The wall section 76 limits movement of the helmet 61 and head in the direction of the arrow A. Such movement is referred to, in medical terms, as "projection". The upper surface of the brace limits tilting of the head and helmet 61 in the direction indicated by the arrow B.

Both braces illustrated are fabricated using resin and glass fiber or carbon fiber and a fabric such as KEVLAR® which are embedded in the resin. KEVLAR® is the strongest of these materials and is used on the inside of the brace. Thus if the brace does fracture, it fractures preferentially on the outside. Any fragments that break off are thus outside the brace and not adjacent the wearer's neck.

The braces are fabricated in such manner that certain zones are weaker than the remainder of the structure of the brace. In the event of an impact, these zones collapse before any other parts of the brace and absorb the forces exerted as a result of the impact. The fracture zones are marked FZ in FIGS. 1 to 6. The same zones exist in the brace of FIGS. 7 to 12.

These zones are created by, for example, using fabric of lesser strength, by making the zones thinner than the surrounding parts of the brace, or by configuring the brace such that fracturing naturally occurs at the desired zones.

The braces described are intended to be worn not by a person who has suffered a neck injury but by a person whose activities increase the chances that a neck injury will be suffered.

By providing a rigid sub-structure of resin covered with cushioning material, and building fracture zones into the rigid sub-structure, it is possible to minimise the transmission of impact shocks to the wearer's neck region by absorbing the shocks. The lip 38, which forms a forward extension of the ring, controls forward tilting movement of the helmeted head. The lower edge of the rear part of the helmet 61 is adjacent the sloping face 76.1 of the wall section 76 and limits both projection and tilting of the helmeted head. Finally the surfaces 20.2 of the top flanges which lie on opposite sides of the neck (see particularly FIGS. 1 and 11) inhibit sideways movement of the head by contact between themselves and the helmet 61.

What is claimed is:

1. A neck brace, comprising:
a ring adapted to encircle a wearer's neck and provide a clearance between the ring and a front lower rim of a full face helmet when the helmet is worn by the wearer, the clearance allowing a range of freedom of movement of the helmet above the ring, the ring comprising:
a front section constructed and arranged to limit forward tilt of the helmet through contact of the front lower rim of the helmet with the front section of the ring, and
a rear section constructed and arranged to limit rearward tilt of the helmet through contact of a rear lower rim of the helmet with the rear section of the ring;
a lower forward extension coupled to the ring and having sufficient rigidity to transfer to the wearer's chest at least some of a force applied to the front section of the ring by the front lower rim of the helmet;
a lower rearward extension coupled to the ring and having sufficient rigidity to transfer to the wearer's back at least some of a force applied to the rear section of the ring by the rear lower rim of the helmet; and
a rigid wall that couples the ring and the lower forward extension.

2. The neck brace of claim 1, wherein the ring comprises two U-shaped sections.

3. The neck brace of claim 2, wherein the U-shaped sections are configured to releasably latch together.

4. The neck brace of claim 1, wherein the ring extends outwardly beyond the rigid wall.

5. The neck brace of claim 1, wherein the ring further has a side surface constructed and arranged to limit sideward tilt of the helmet through contact of a side lower rim of the helmet and the side surface of the ring.

6. The neck brace of claim 1, further comprising:
a first fracture zone adjacent the front section, configured to collapse prior to the remainder of the brace collapsing in response to a force applied to the front section of the ring by the lower rim of the helmet, thereby absorbing at least some of the force.

7. The neck brace of claim 6, wherein the rear section includes an upwardly extending rear surface constructed and arranged to limit rearward tilt of the helmet through contact of the rear lower rim of the helmet and the upwardly extending rear surface.

8. The neck brace of claim 7, further comprising:
a second fracture zone adjacent the upwardly extending rear surface, the second fracture zone configured to collapse prior to the remainder of the brace collapsing in in response to a second force applied to the upwardly facing rear surface of the ring by the rear lower rim of the helmet, thereby absorbing at least some of the second force.

9. The neck brace of claim 8, wherein at least one of the first and second fracture zones is formed by using one or more materials collectively having a strength that is less than the strength of the materials forming the remainder of the brace.

10. The neck brace of claim 8, wherein at least one of the first and second fracture zones has walls that are thinner than the walls forming the remainder of the brace.

11. The neck brace of claim 1, wherein the lower rearward extension includes a column extending from the ring down the wearer's back.

12. The neck brace of claim 11, wherein the column is configured for transferring the forces to the wearer's back adjacent the spine.

13. A neck brace, comprising:
a front section having a first upwardly facing surface;
a rear section having a second upwardly facing surface and constructed and arranged to releasably couple to the front section, such that the neck of a wearer is encircled and such that a helmet having a full face and worn by the user has lateral rotation above the front and rear sections;
a front downward extension coupled to the front section and having sufficient rigidity to transfer to the wearer's front at least some of a force applied to the first upwardly facing surface by the front lower rim of the helmet; and
a rear downward extension coupled to the rear section and having sufficient rigidity to transfer to the wearer's back at least some of a force applied to the second upwardly facing surface by a rear lower rim of the helmet.

14. The neck brace of claim 13, further comprising:
a rigid wall that extends between the ring and the front downward extension.

15. The neck brace of claim 14, wherein the first upwardly facing surface extends outwardly beyond the rigid wall.

16. The neck brace of claim 13, further comprising:
a first fracture zone adjacent the first upwardly facing surface, configured to collapse prior to the remainder of the brace collapsing in response to a force applied to the first upwardly facing surface by the front lower rim of the helmet, thereby absorbing at least some of the force.

17. The neck brace of claim 16, further comprising:
a second fracture zone adjacent the second upwardly facing surface, the second fracture zone configured to collapse prior to the remainder of the brace collapsing in response to a second force applied to the second upwardly facing surface by the rear lower rim of the helmet, thereby absorbing at least some of the second force.

18. The neck brace of claim 17, wherein at least one of the first and second fracture zones is formed by using one or more materials collectively having a strength that is less than the strength of the materials forming the remainder of the brace.

19. The neck brace of claim 17, wherein at least one of the first and second fracture zones has walls that are thinner than the walls forming the remainder of the brace.

20. The neck brace of claim 13, wherein the rear downward extension includes a column extending from the ring down the wearer's back.

21. The neck brace of claim 20, wherein the column is configured for transferring the forces to the wearer's back adjacent the spine.

22. A neck brace comprising:
a ring constructed and arranged to encircle a wearer's neck and provide a clearance between the ring and a front lower rim of a helmet having a full face when the helmet is worn by the wearer, the clearance allowing a range of freedom of movement of the helmet above the ring, the ring including,
a front generally upwardly facing impact surface constructed and arranged to limit forward tilt of a helmet through contact of the front lower rim of the full face of the helmet with the front generally upwardly facing impact surface of the ring; and
a rear generally upwardly facing impact surface constructed and arranged to limit rearward tilt of the helmet through contact of the rear lower rim of the helmet with the rear generally upwardly facing impact surface of the ring;
a lower forward extension coupled to the ring and having sufficient rigidity to transfer to the wearer's front at least some of a force applied to the front generally upwardly facing impact surface by the front lower rim of the full face of the helmet;
a lower rearward extension coupled to the ring and having sufficient rigidity to transfer to the wearer's back at least some of a force applied to the rear generally upwardly facing impact surface by the rear lower rim of the helmet; and
a rigid wall that extends between the ring and the lower forward extension.

23. The neck brace of claim 22, wherein the front generally upwardly facing impact surface extends outwardly beyond the rigid wall.

24. The neck brace of claim 22, wherein the ring comprises two U-shaped sections.

25. The neck brace of claim 24, wherein the U-shaped sections are configured to releasably latch together.

26. The neck brace of claim 22, further comprising:
a fracture zone adjacent the front upwardly facing surface, configured to collapse prior to the remainder of the brace collapsing in response to a force applied to the first upwardly facing surface by the front lower rim of the helmet, thereby absorbing at least some of the force.

27. The neck brace of claim 26, further comprising:
a fracture zone adjacent the rear upwardly facing surface, the fracture zone configured to collapse prior to the remainder of the brace collapsing in response to a force applied to the rear upwardly facing surface by the rear lower rim of the helmet, thereby absorbing at least some of the second force.

28. A neck brace, comprising:
a ring adapted to encircle a wearer's neck and provide a clearance between the ring and a front lower rim of a full face helmet when the helmet is worn by the wearer, the clearance allowing a range of freedom of movement of the helmet above the ring, the ring comprising:
a front section constructed and arranged to limit forward tilt of the helmet through contact of the front lower rim of the helmet with the front section of the ring, and
a rear section constructed and arranged to limit rearward tilt of the helmet through contact of a rear lower rim of the helmet with the rear section of the ring;
a lower forward extension coupled to the ring and having sufficient rigidity to transfer to the wearer's chest at least some of a force applied to the front section of the ring by the front lower rim of the helmet;
a lower rearward extension coupled to the ring and having sufficient rigidity to transfer to the wearer's back at least some of a force applied to the rear section of the ring by the rear lower rim of the helmet; and wherein the ring further has a side surface constructed and arranged to limit sideward tilt of the helmet through contact of a side lower rim of the helmet and the side surface of the ring.

29. The neck brace of claim 28, wherein the ring comprises two U-shaped sections.

30. The neck brace of claim 29, wherein the U-shaped sections are configured to releasably latch together.

31. The neck brace of claim 28, further comprising:
a rigid wall that couples the ring and the lower forward extension.

32. The neck brace of claim 31, wherein the ring extends outwardly beyond the rigid wall.

33. The neck brace of claim 28, further comprising:
a first fracture zone adjacent the front section, configured to collapse prior to the remainder of the brace collapsing in response to a force applied to the front section of the ring by the lower rim of the helmet, thereby absorbing at least some of the force.

34. The neck brace of claim 33, wherein the rear section includes an upwardly extending rear surface constructed and arranged to limit rearward tilt of the helmet through contact of the rear lower rim of the helmet and the upwardly extending rear surface.

35. The neck brace of claim 34, further comprising:
a second fracture zone adjacent the upwardly extending rear surface, the second fracture zone configured to collapse prior to the remainder of the brace collapsing in response to a second force applied to the upwardly facing rear surface of the ring by the rear lower rim of the helmet, thereby absorbing at least some of the second force.

36. The neck brace of claim 35, wherein at least one of the first and second fracture zones is formed by using one or more materials collectively having a strength that is less than the strength of the materials forming the remainder of the brace.

37. The neck brace of claim 35, wherein at least one of the first and second fracture zones has walls that are thinner than the walls forming the remainder of the brace.

38. The neck brace of claim 28, wherein the lower rearward extension includes a column extending from the ring down the wearer's back.

39. The neck brace of claim 38, wherein the column is configured for transferring the forces to the wearer's back adjacent the spine.

40. A neck brace, comprising:
a ring adapted to encircle a wearer's neck and provide a clearance between the ring and a front lower rim of a full face helmet when the helmet is worn by the wearer, the clearance allowing a range of freedom of movement of the helmet above the ring, the ring comprising:
a front section constructed and arranged to limit forward tilt of the helmet through contact of the front lower rim of the helmet with the front section of the ring, and
a rear section constructed and arranged to limit rearward tilt of the helmet through contact of a rear lower rim of the helmet with the rear section of the ring;
a lower forward extension coupled to the ring and having sufficient rigidity to transfer to the wearer's chest at least some of a force applied to the front section of the ring by the front lower rim of the helmet;
a lower rearward extension coupled to the ring and having sufficient rigidity to transfer to the wearer's back at least some of a force applied to the rear section of the ring by the rear lower rim of the helmet, wherein the lower rearward extension includes a column extending from the ring down the wearer's back.

41. The neck brace of claim 40, wherein the ring comprises two U-shaped sections.

42. The neck brace of claim 41, wherein the U-shaped sections are configured to releasably latch together.

43. The neck brace of claim 40, further comprising:
a rigid wall that couples the ring and the lower forward extension.

44. The neck brace of claim 43, wherein the ring extends outwardly beyond the rigid wall.

45. The neck brace of claim 40, wherein the ring further has a side surface constructed and arranged to limit sideward tilt of the helmet through contact of a side lower rim of the helmet and the side surface of the ring.

46. The neck brace of claim 40, further comprising:
a first fracture zone adjacent the front section, configured to collapse prior to the remainder of the brace collapsing in response to a force applied to the front section of the ring by the lower rim of the helmet, thereby absorbing at least some of the force.

47. The neck brace of claim 46, wherein the rear section includes an upwardly extending rear surface constructed and arranged to limit rearward tilt of the helmet through contact of the rear lower rim of the helmet and the upwardly extending rear surface.

48. The neck brace of claim 47, further comprising:
a second fracture zone adjacent the upwardly extending rear surface, the second fracture zone configured to collapse prior to the remainder of the brace collapsing in in response to a second force applied to the upwardly facing rear surface of the ring by the rear lower rim of the helmet, thereby absorbing at least some of the second force.

49. The neck brace of claim 48, wherein at least one of the first and second fracture zones is formed by using one or more materials collectively having a strength that is less than the strength of the materials forming the remainder of the brace.

50. The neck brace of claim 48, wherein at least one of the first and second fracture zones has walls that are thinner than the walls forming the remainder of the brace.

51. The neck brace of claim 40, wherein the column is configured for transferring the forces to the wearer's back adjacent the spine.

* * * * *